United States Patent
Buchalova et al.

(10) Patent No.: US 10,441,557 B2
(45) Date of Patent: *Oct. 15, 2019

(54) GERMICIDAL COMPOSITIONS COMPRISING CARBOXYLIC ACID MIXTURE AND USE AS TOPICAL DISINFECTANTS

(71) Applicant: DeLaval Holding AB, Tumba (SE)

(72) Inventors: Maria Buchalova, Lawrence, KS (US); Alex Skender, Kansas City, MO (US)

(73) Assignee: DeLaval Holding AB, Tumba (SE)

( * ) Notice: Subject to any disclaimer, the term of this patent is extended or adjusted under 35 U.S.C. 154(b) by 153 days.

This patent is subject to a terminal disclaimer.

(21) Appl. No.: 14/653,174

(22) PCT Filed: Dec. 20, 2013

(86) PCT No.: PCT/SE2013/051588
§ 371 (c)(1),
(2) Date: Jun. 17, 2015

(87) PCT Pub. No.: WO2014/098759
PCT Pub. Date: Jun. 26, 2014

(65) Prior Publication Data
US 2015/0335598 A1 Nov. 26, 2015

Related U.S. Application Data

(60) Provisional application No. 61/745,174, filed on Dec. 21, 2012, provisional application No. 61/783,056, filed on Mar. 14, 2013.

(51) Int. Cl.
| | | |
|---|---|---|
| A61K 31/194 | (2006.01) | |
| A01N 37/02 | (2006.01) | |
| A61K 9/00 | (2006.01) | |
| A61K 31/185 | (2006.01) | |
| A61K 31/19 | (2006.01) | |
| A61K 45/06 | (2006.01) | |
| A61K 47/20 | (2006.01) | |

(52) U.S. Cl.
CPC ............ *A61K 31/194* (2013.01); *A01N 37/02* (2013.01); *A61K 9/0017* (2013.01); *A61K 31/185* (2013.01); *A61K 31/19* (2013.01); *A61K 45/06* (2013.01); *A61K 47/20* (2013.01)

(58) Field of Classification Search
CPC .................................................... A61K 31/194
See application file for complete search history.

(56) References Cited

U.S. PATENT DOCUMENTS

2010/0234460 A1* 9/2010 Foret ...................... A01N 37/02
514/558

FOREIGN PATENT DOCUMENTS

| EA | 200602094 | 4/2007 |
|---|---|---|
| EP | 1304031 | 4/2003 |
| RU | 2224547 | 10/2004 |
| WO | 1998000009 | 8/1998 |
| WO | 2000013506 | 9/1998 |
| WO | 0194513 | 12/2001 |
| WO | 2008031087 | 3/2008 |

OTHER PUBLICATIONS

The International Search Report and Written Opinion dated Apr. 23, 2014, in PCT/SE2013/051588, filed Dec. 20, 2013.
The Office Action dated Nov. 28, 2017, issued in RU 2015129702 filed Dec. 20, 2013.
The First Examination Report dated Aug. 22, 2018, in NZ Patent Application No. 708453.

* cited by examiner

*Primary Examiner* — Jeffrey S Lundgren
*Assistant Examiner* — Tori Strong
(74) *Attorney, Agent, or Firm* — Hovey Williams LLP

(57) ABSTRACT

Germicidal compositions and methods of using the same in the prevention and treatment of various hoof diseases are provided. The germicidal compositions generally comprise formic acid, at least one C2-C10 carboxylic acid, and one or more anionic surfactants, such as an α-olefin sulfonate. The germicidal compositions may be applied topically to the hooves of an animal through various means including the use of footbaths.

21 Claims, 4 Drawing Sheets

GERMICIDAL COMPOSITIONS COMPRISING CARBOXYLIC ACID MIXTURE AND USE AS TOPICAL DISINFECTANTS

RELATED APPLICATIONS

This is a national stage application under 35 U.S.C. § 371 of International Application No. PCT/SE2013/051588, filed Dec. 20, 2013, which claims benefit of U.S. Provisional Patent Application Nos. 61/745,174, filed Dec. 21, 2012 and 61/783,056, filed Mar. 14, 2013, all of which are hereby incorporated by reference herein in their entireties.

BACKGROUND OF THE INVENTION

Field of the Invention

The present invention relates to compositions and methods of using the same as topical disinfectants, particularly for the control of hoof diseases. In particular, solutions effective in treating or preventing papillomatous digital dermatitis, interdigital phlegmon, interdigital dermatitis, laminitis, white line disease, heel erosion and other hoof diseases are disclosed.

Description of the Prior Art

Infectious diseases of the hooves, such as hairy hoof warts (papillomatous digital dermatitis, or "PDD"), hoof rot (interdigital phlegmon), stable hoof rot (interdigital dermatitis), laminitis, white line disease and heel erosion are common in farm animals such as sheep, goats, horses, dairy cows and beef cattle. These diseases are a significant source of lameness, and produce a large economic and humane impact on the farming industry.

PDD is an infection of the epidermis of an animal's digit that is believed to be caused by *Treponema* organisms, which survive under the skin in conditions of low oxygen, temperatures between 30° C. and 37° C., and a pH range of 7.2 to 7.4. PDD infections range from painful, moist lesions to raised, hairy, wart-like lesions that can result in severe lameness, and even death, if not properly treated. With respect to dairy cows, hoof warts are also associated with losses in milk production, reproductive efficiency and body weight. Hoof rot, or interdigital phlegmon, is an infection of the soft tissue between the claws of the feet, where bacteria invade the skin of the foot at injured or damaged skin areas. Initially, the infection causes a painful swelling of the skin between the claws. A fissure or crack then develops along the swollen area for part or all of the length of the interdigital space. If left untreated, hoof rot can enter the joints, bones, and/or tendons of the foot, making recovery from the infection unlikely. Animals with hoof rot can have a mild fever, loss of appetite and accompanying weight loss, and develop mild to severe lameness. Interdigital dermatitis, or stable hoof rot, is generally a chronic inflammation of the skin in the interdigital cleft. The condition may cause lameness or heel crack/heel erosion. These three hoof diseases—papillomatous digital dermatitis, interdigital phlegmon and interdigital dermatitis—are caused by bacterial infections, and they may be accompanied by or lead to complications with other hoof diseases such as laminitis, white line disease and heel erosion.

Treatment or prevention of hoof diseases generally involves topical application of antibiotics to affected areas. However, antibiotics are expensive, and, particularly when treating cattle, concerns related to the presence of antibiotics in beef and milk arise. Further, it is well known that extended use of antibiotics leads to antibiotic-resistance, and the development of more aggressive strains of bacteria.

The use of chemical germicides to treat or prevent hoof diseases is also common. For example, germicidal compositions containing copper sulfate, zinc sulfate, sulfamethazine, quaternary ammonium compounds, hydrogen peroxide and/or peracetic acid are known.

Application of the antibiotic or germicidal compositions is typically carried out by making the animals walk through a footbath. However, after a few animals have passed through the footbath, the solution becomes contaminated with manure. Many formulas that are currently used for footbath solutions lose their activity in the presence of manure. As a result, these baths can become a breeding ground for bacteria, and can accelerate the spread of infectious hoof diseases, rather than prevent them. Infectious hoof diseases can also be treated by a topical spray, or application of a foam or gel or application of a topical antimicrobial liquid, paste, gel or spray followed by covering with a protective footwrap. However, the hoof is likely to be highly contaminated with manure, dirt or other soils before and/or shortly after application.

Other germicides, especially oxidative germicides such as iodine, chlorine, chlorine dioxide, hydrogen peroxide or peracetic acid are extremely effective disinfectants for other purposes, but they are not useful for a footbath solution because they quickly react with manure, which reduces the efficacy of the active ingredients. Germicides such as salicylic acid are also ineffective for footbath solutions due to limited solubility.

SUMMARY OF THE INVENTION

According to one embodiment of the present invention there is provided an aqueous germicidal composition comprising formic acid, one or more C2-C10 carboxylic acids, and one or more anionic surfactants. Particularly, the germicidal composition comprises between about 0.05% to about 35% by weight formic acid and between about 0.05% to about 35% by weight of the one or more C2-C10 carboxylic acids. Exemplary carboxylic acids for use with the present invention include acetic acid, lactic acid, and citric acid. Exemplary anionic surfactants that are particularly suitable for use with the present invention include α-olefin sulfonate surfactants, especially sodium C8-C18 olefin sulfonates.

The germicidal compositions may be prepared as concentrates suitable for dilution with water immediately prior to use, or they may be prepared as ready-to-use formulations. In certain embodiments, the germicidal composition is provided as a concentrate and diluted with between 1 to 100 parts by weight water to form a use solution.

In another embodiment according to the present invention there is provided a method for treating or preventing infectious hoof diseases comprising topically administering to the hooves of an animal a therapeutically effective amount of a germicidal composition as described herein. Because certain germicidal compositions according to the present invention maintain a high degree of efficacy even under relatively high soil loadings, pre-washing of the animal hooves to remove such soils (e.g., manure) can be reduced or avoided. In certain embodiments, the germicidal composition may be applied as a footbath, although, any number of alternative means of application are acceptable including application by topical spray, direct application of a liquid solution, application of a gel, paste or ointment.

DETAILED DESCRIPTION OF THE PREFERRED EMBODIMENT

Figure 1:
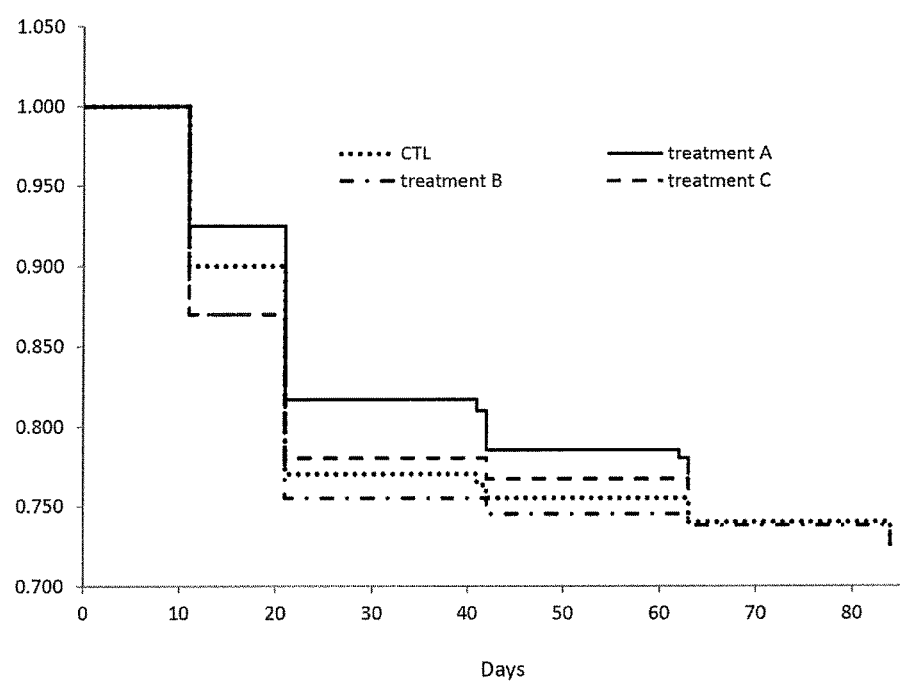
FIG. 1 is a Kaplan-Meier survival graph illustrating the results of a digital dermatitis (DD) study in terms of the probably of DD at the cow level at different times after enrollment.

While the use of topical germicidal compositions in the treatment of various skin conditions and diseases is well established, treatment of agricultural animals, such as bovine, presents some unique challenges. In the context of hoof diseases, many conventional germicidal compositions are simply ineffective when applied to animal hooves in their natural state. By "natural state" it is meant that the hooves of the animal have not been washed or pre-treated to remove organic soils, such as manure, that may become deposited on the hooves through the natural or routine activities of the animal. Such organic soils deposited on the outer surface of the hooves can deactivate a number of conventional antimicrobial agents. Accordingly, the antimicrobial agent may not sufficiently contact the affected portion of the animal so as to provide the necessary prophylactic or therapeutic effect. In order to combat this issue, additional efforts must be undertaken to remove as much of the organic soils from the hooves as possible. However, even the best efforts in this regard can fall short leading to a number of unprotected animals and putting the health of the entire herd at risk.

A number of germicidal agents have also come under closer scrutiny by regulatory authorities as being potential environmental hazards. Copper sulfate, for example, is a particular concern as it has been classified by the U.S. EPA as being in toxicity class I—highly toxic—and has been implicated as a contributor to certain types of water pollution. Thus, the use of copper sulfate as an antimicrobial agent in hoof baths, which often have the tendency to spill from the hoof bath as the animal wades through and run off into the environment, is becoming quite disfavored.

The present invention provides germicidal compositions and methods of using the same in the prevention and treatment of hoof diseases, while reducing the risks associated with conventional treatments. In certain embodiments, the germicidal compositions comprise formic acid, at least one C2-C10 carboxylic acid, and one or more anionic surfactants. The germicidal compositions may be provided as a concentrate that is diluted with water to form a use solution prior to application to the animal hoof or as a ready-to-use formulation for direct application to the animal. The ready to use formulation may be low or high viscosity liquid, paste, or gel.

Formic acid may comprise between about 0.05% to about 35% by weight, between about 0.1% to about 30% by weight, or between about 0.2% to about 25% by weight of the germicidal composition. In certain embodiments, where the composition is provided as a concentrate, formic acid may be present at a level of between about 2% to about 35% by weight, between about 4% to about 30% by weight, or between about 6% to about 25% by weight. In certain embodiments, where the composition is provided in ready-to-use form or is a use solution formed from dilution of a concentrate, formic acid may be present at a level of between about 0.05% to about 5% by weight, between about 0.1% to about 2.5% by weight, or between about 0.2% to about 1.25% by weight.

Compositions according to the present invention also comprise one or more C2-C10 carboxylic acids. In certain preferred embodiments, the one or more carboxylic acids comprise C2-C6 carboxylic acids. The carboxylic acids may be saturated or unsaturated, and contain a single carboxylic acid functional group or a plurality of carboxylic acid functional groups, such as two or three. In particular embodiments, the one or more carboxylic acids are selected from the group consisting of acetic acid, lactic acid, citric acid, propionic acid, butyric acid, glycolic acid, gluconic acid, glutaric acid, adipic acid, aspartic acid, glutamic acid, tartaric acid, pyruvic acid, fumaric acid, sorbic acid, maleic acid, and malic acid. If a longer alkyl chain fatty acids are desired, exemplary C8-C10 carboxylic acids that may be used with the present invention include caprylic acid, pelargonic acid, and capric acid. Generally, the one or more C2-C10 carboxylic acids are present in the germicidal composition at a level of between about 0.05% to about 35% by weight, between about 0.1% to about 30% by weight, or between about 0.2 to about 25% by weight. In certain embodiments, where the composition is provided as a concentrate, the one or more C2-C10 carboxylic acids may be present at a level of between about 2% to about 35% by weight, between about 4% to about 30% by weight, or between about 6% to about 25% by weight. In certain embodiments, where the composition is provided in ready-to-use form or is a use solution formed from dilution of a concentrate, the one or more C2-C10 carboxylic acids may be present at a level of between about 0.05% to about 5% by weight, between about 0.1% to about 2.5% by weight, or between about 0.2% to about 1.25% by weight.

Carboxylic acids comprise a significant portion of the germicidal compositions according to the present invention. Generally, the total carboxylic acid concentration, including formic and any other C2-C10 carboxylic acids, is between about 0.1 to about 70% by weight, between about 0.2% to about 60% by weight, or between about 0.45% to about 50% by weight. In certain embodiments, where the composition is provided as a concentrate, the total carboxylic acid concentration is between about 4% to about 70% by weight, between about 8% to about 60% by weight, or between about 12 to about 50% by weight. In certain embodiments, where the composition is provided in ready-to-use form or is a use solution formed from dilution of a concentrate, the total carboxylic acid concentration is between about 0.1% to about 10%, between about 0.2% to 5%, or between about 0.45% to about 2.5%.

Compositions according to the present invention also comprise one or more anionic surfactants. In certain embodiments, the one or more anionic surfactants may be selected from the group consisting of alkyl sulfates, such as sodium lauryl sulfate; alkenyl sulfates; alkyl or alkenyl aryl sulfates; alkyl or alkenyl aryl sulfonates; alkyl sulfonates, such as sodium octane sulfonate; and alkenyl sulfonates. In still other embodiments, the one or more anionic surfactants may be selected from the group consisting of alkyl sulfonic acids, an alkyl sulfonate salts, a linear alkyl benzene sulfonic acids, a linear alkyl benzene sulfonates, an alkyl α-sulfomethyl ester, α-olefin sulfonates, alcohol ether sulfates, alkylsulfo succinates, dialkylsulfo succinates, or alkali metal, alkaline earth metal, amine and ammonium salts thereof. Specific examples of anionic surfactants suitable for use with the present invention include linear C10-C16 alkylbenzene sulfonic acid, linear C10-C16 alkylbenzene sulfonates or alkali metal, alkaline earth metal, amine and ammonium salts thereof, e.g., sodium dodecylbenzene sulfonate, sodium C8-C18 α-olefin sulfonates (e.g., sodium C12-C18 α-olefin sulfonate and C14-C16 α-olefin sulfonate), sodium methyl α-sulfomethyl ester, disodium methyl α-sulfo fatty acid salts, sodium laureth sulfate and dioctyl sodium sulfosuccinate. In the composition of the present invention the anionic surfactant may be present as either the salt or acid form depending on the pH of the composition. Generally, the one or more anionic surfactants are present in the germicidal composition at a level of between about 0.1% to about 60% by weight, between about 0.25% to about 55%, or between about 0.5 to about 50% by weight. In certain embodiments, where the composition is provided as a concentrate, the one or more anionic surfactants may be present at a level of between about 3% to about 60% by weight, between about 5% to about 55% by weight, or between about 20% to about 50% by weight. In certain embodiments, where the composition is provided in ready-to-use form or is a use solution formed from dilution of a concentrate, the one or more anionic surfactants may be present at a level of between about 0.1% to about 5% by weight, between about 0.25% to about 2.5% by weight, or between about 0.5% to about 1% by weight.

In certain embodiments of the present invention, the use of anionic surfactant blends (e.g., two or more of the aforementioned anionic surfactants) can result in improved low temperature performance of the concentrate and improved stability of use solution formulations in the presence of low organic soil (3 g/L bovine albumin). For example, improved physical stability of the formulation, that is, the lack of precipitate formation, at temperatures at or below 0° C. can be achieved in this manner. In particular embodiments, an α-olefin sulfonate comprises the primary anionic surfactant present in the blend. More specifically, the α-olefin sulfonate comprises at least 50%, at least 60% or at least 70% by weight of the total anionic surfactant present in the formulation, with the balance of the blend being made up of one or more additional anionic surfactants.

Certain embodiments according to the present invention may further comprise an additional surfactant separate from the aforementioned one or more anionic surfactants. In particular embodiments, this further surfactant comprises a nonionic surfactant. Exemplary nonionic surfactants include alkyl polyglucosides, alkyl ethoxylated alcohols, alkyl propoxylated alcohols, ethoxylated-propoxylated alcohols, sorbitan, sorbitan esters, and alkanol amides. Additional specific exemplary nonionic surfactants include C8-C16 alkyl polyglucosides with a degree of polymerization ranging from 1 to 3, e.g., C8-C10 alkyl polyglucoside with a degree of polymerization of 1.5 (Glucopon® 200), C8-C16 alkyl polyglucoside with a degree of polymerization of 1.45 (Glucopon® 425), C12-C16 alkyl polyglucoside with a degree of polymerization of 1.6 (Glucopon® 625), and polyethoxylated polyoxypropylene block copolymers (poloxamers) including by way of example the Pluronic® poloxamers commercialized by BASF Chemical Co. In particular embodiments, the nonionic surfactant comprises a primary alcohol ethoxylate, such as Neodol® 91-6, which is based on a C9-C11 alcohol with an average of approximately 6 moles of ethylene oxide per mole of alcohol, or C9-C11 pareth-8, which has an average of about 8 moles of ethylene oxide per mole of alcohol. Generally, the additional surfactant may be present in compositions according to the present invention at a level of between about 0.01% to about 20% by weight, between about 0.05% to about 15% by weight, or between about 0.1% to about 10% by weight. In certain embodiments, where the composition is provided as a concentrate, the additional surfactant may be present at a level of between about 0.5% to about 20% by weight, between about 1% to about 15% by weight, or between about 2% to about 10% by weight. In certain embodiments, where the composition is provided in ready-to-use form or is a use solution formed from dilution of a concentrate, the additional surfactant may be present at a level of between about 0.01% to about 5% by weight, between about 0.05% to about 2.5% by weight, or between about 0.1% to about 1% by weight.

In certain embodiments, compositions according to the present invention may comprise an additional germicide, different from the aforementioned components, in an amount up to about 25% by weight. Exemplary suitable germicides include N,N-bis(3-aminopropyl) C6-C18 alkyl amines (such as N,N-bis(3-aminopropyl)dodecylamine), bronopol (2-bromo-2-nitro-1,3-propanediol), chlorhexidine salts, triclosan (2,4,4'-trichloro-2'-hydroxydiphenylether, from Ciba Specialty Chemicals as IRGASAN and IRGASAN DP 300), glycolic acid, benzyl alcohol, benzoic acid, polyhexamethyl biguanide (CAS 32289-58-0), guanidine salts such as polyhexamethylene guanidine hydrochloride (CAS 57028-96-3), polyhexamethylene guanidine hydrophosphate (89697-78-9), and poly[2-(2-ethoxy)-ethoxyethyl]-guanidinium chloride (CAS 374572-91-5), iodine-containing compounds, and mixtures thereof.

In other embodiments, the compositions may include various traditional germicides such as copper sulfate, zinc sulfate, sulfamethazine, quaternary ammonium compounds, hydrogen peroxide and/or peracetic acid. However, it is also within the scope of the present invention to avoid the use of certain traditional germicides. Thus, in some embodiments, the compositions do not comprise any of the foregoing additional germicides, and especially, do not comprise iodine, chlorhexidene, or copper sulfate. In still other embodiments, it may be preferable for the compositions to avoid the use of traditional fatty acid germicides, such as C8-C14 fatty acid germicides.

In addition to the carboxylic acids discussed above, mineral acids having efficacy against microorganisms, particularly bacteria, and minimal irritation of the skin may be incorporated into the present compositions. Examples of suitable mineral acids include sulfuric acid, sulfurous acid, sulfamic acid, hydrochloric acid, phosphoric acid, and phosphorous acid. Acids such as methane sulfonic acid may also be used.

Compositions according to the present invention may optionally comprises one or more members selected from the group consisting of pH adjusting agents, wetting agent, foaming agents, dyes, viscosity control agents, preservatives, skin conditioners, coupling agents, and solvents.

pH Adjusting Agents

It will be appreciated that compositions according to the present invention comprise at least two carboxylic acids, with one being formic acid. The presence of those acids will affect the pH of the composition. The pH of the composition may, however, be adjusted by the addition of acidic, basic or buffering agents. Suitable acids for use as pH adjusting agents may include, for example, sulfuric acid, sulfurous acid, sulfamic acid, hydrochloric acid, phosphoric acid, phosphorous acid, glycolic acid, benzoic acid, malic acid, oxalic acid, tartaric acid, succinic acid, glutaric acid, valeric acid, and the like. The pH may be raised, or made more alkaline, by addition of an alkaline agent such as sodium hydroxide, ammonium hydroxide, potassium hydroxide, sodium carbonate, sodium bicarbonate, monosodium acid diphosphonate or combinations thereof.

Wetting Agents

Wetting agents may be included in the disclosed formulations. Typical wetting agents are used to wet the surface of application, thereby reducing surface tension so that the product can easily contact the surface. The wetting agents of the formulation increase overall detergency of the formula, solubilize or emulsify organic ingredients that otherwise would not dissolve or emulsify, and facilitate penetration of active ingredients deep into depressions of the surface, which may be an animal hoof.

Suitably effective wetting agents may include anionic, nonionic, zwitterionic and amphoteric surfactants. Wetting agents and surfactants suitable for use in the disclosed formulations can be high foaming, low foaming and non-foaming. Suitable anionic surfactants include alkyl sulfonic acids, alkyl sulfonate salts, linear alkyl benzene sulfonic acids, linear alkyl benzene sulfonates, alkyl α-sulfomethyl esters, α-olefin sulfonates, alcohol ether sulfate, alkyl sulfates, alkylsulfo succinates, dialkylsulfo succinates, or alkali metal, alkaline earth metal, amine and ammonium salts thereof. Specific examples are linear C10-C16 alkylbenzene sulfonic acids, linear C10-C16 alkylbenzene sulfonates or alkali metal, alkaline earth metal, amine and ammonium salts thereof, e.g., sodium dodecylbenzene sulfonate, sodium C14-C16 α-olefin sulfonate, sodium methyl α-sulfomethyl ester, and disodium methyl α-sulfo fatty acid salts. Suitable nonionic surfactants include alkyl polyglucosides, alkyl ethoxylated alcohols, alkyl propoxylated alcohols, ethoxylated-propoxylated alcohols, sorbitan, sorbitan esters, and alkanol amides. Specific examples include C8-C16 alkyl polyglucosides with a degree of polymerization ranging from 1 to 3, e.g., C8-C10 alkyl polyglucosides with a degree of polymerization of 1.5 (Glucopon® 200), C8-C16 alkyl polyglucosides with a degree of polymerization of 1.45 (Glucopon® 425), C12-C16 alkyl polyglucosides with a degree of polymerization of 1.6 (Glucopon® 625), and polyethoxylated polyoxypropylene block copolymers (poloxamers) including by way of example the Pluronic® poloxamers commercialized by BASF Chemical Co. Exemplary amphoteric surfactants include alkyl betaines and alkyl amphoacetates. Suitable betaines include cocoamidopropyl betaine, and suitable amphoacetates include sodium cocoamphoacetate, sodium lauroamphoacetate and sodium cocoamphodiacetate.

Foaming Agents

The germicidal compositions may further comprise a foaming agent. A foaming agent aerates a liquid composition to produce a foam that may increase surface area of the composition and improve adherence with the surface to be treated (e.g., an animal hoof). Typically, a high foaming surfactant such as sodium lauryl sulfate, dodecylbenzene sulfonic acid, sodium alkylaryl polyether sulfate, sodium lauryl ether sulfate, sodium decyl sulfate, cocamine oxide, C12-C14 whole coconut amido betaines can be used to generate a stable foam. The foam is produced when agitation in the form of a compressed gas is mixed with the solution either by bubbling the gas into the solution or spraying the solution or solution-gas mixture through spray equipment. Suitable gases include but are not limited to nitrogen, air, carbon dioxide and mixtures thereof. Foam can also be generated by the mechanical action of animals walking through the composition, or by other mechanical means that mix atmospheric air with the composition. The composition can be applied by having animals walk through an area containing the foam or by having the animal walk through a footbath solution that has foam floating on top of the solution.

Dyes

One or more dyes may be included in the composition. Color on an animal's hoof or hooves may serve as a visual indicator that a particular animal has been treated. To preclude any problems with possible contamination of milk, for example, in the event that the dye contacts the animal's teats or enters the animal's circulatory system, only FD&C Certified (food grade) dyes should be used. There are many FD&C dyes available, such as FD&C Red #40, FD&C Yellow #6, FD&C Yellow #5, FD&C Green #3, FD&C Blue #1, FD&C Orange #4 and combinations thereof.

Viscosity Modifying Agents

Solution viscosity may be thinned by the addition of water or co-solvent; however, the compositions, especially gel forms, may benefit from the use of a viscosity modifying agent in an amount generally ranging from 0.1% to about 10% by weight of the composition. Viscosity of the composition preferably ranges from 1 cPs to 10000 cPs at ambient temperature. The viscosity referred to throughout this application is Brookfield viscosity measured in cPs by a Brookfield LV viscometer at ambient temperature (25° C.) with a spindle #2@ 3 to 30 rpm. In various embodiments, a thickener may be added to achieve a viscosity range of from 50 cPs to 10000 cPs, or from 1000 cPs to 4000 cPs.

Viscosity modifying agents include plant gum materials such as guar gum; starch and starch derivatives, for example, hydroxyethyl starch or cross-linked starch; microbial polysaccharides, for example, xanthan gum or seaweed polysaccharides, such as sodium alginate, carrageenan, curdlan, pullulan or dextran; whey; gelatin; chitosan; chitosan derivatives; polysulfonic acids and their salts; polyacrylamide; and glycerol. Cellulosic thickeners may be used including hemicellulose, for example arabinoxylanes and glucomannanes; cellulose and derivatives thereof, for example methyl cellulose, ethyl cellulose, hydroxyethyl cellulose or carboxymethyl cellulose.

Preservatives

Preservatives may also be added to the compositions. For example, ethylenediaminetetraacetic acid (EDTA) and its alkali salts act as chelating agents to bind metal ions that would otherwise facilitate metalloenzyme reactions that produce energy for bacterial cell replication. Other traditional preservatives may be used, for example, paraban, methyl paraban, ethyl paraban, glutaraldehyde, etc. Preservatives such as an alcohol can also be added. The alcohol, in certain embodiments, may be benzyl alcohol, a low molecular weight alcohol having a carbon number less than five, and combinations thereof.

Skin Conditioning Agents

Compositions according to the present invention may optional comprise skin conditioning agents. Skin conditioning agents may provide extra protection for human or animal skin prior to or subsequent to being exposed to adverse conditions. For example, skin conditioning agents may include moisturizers, such as glycerin, sorbitol, propylene glycol, Laneth-5 to 100, lanolin alcohol, D-panthenol, polyethylene glycol (PEG) 200-10,000, polyethylene glycol esters, acyl lactylates, polyquarternium-7, glycerol cocoate/laurate, PEG-7 glycerol cocoate, stearic acid, hydrolyzed silk peptide, silk protein, guar hydroxypropyltrimonium chloride, alkyl poly glucoside/glyceryl laurate, shea butter and coco butter; sunscreen agents, such as titanium dioxide, zinc oxide, octyl methoxycinnamate (OMC), 4-methylbenzylidene camphor (4-MBC), avobenzone, oxybenzone and homosalate; and itch-relief or numbing agents, such as aloe vera, calamine, mint, menthol, camphor, antihistamines, corticosteroids, benzocaine and paroxamine HCl.

Coupling Agents

In some embodiments, the germicidal compositions may contain a coupling agent that facilitates dissolution of one or more components, e.g., surfactants or fatty acids that would otherwise be insoluble or only sparingly soluble in the solvent. Coupling agents generally contain short chained (C2-C6) moieties linked to bulky hydrophilic groups, such as hydroxyl and/or sulfonate groups. Exemplary coupling agents include aryl sulfonates such as sodium naphthalene sulfonate, sodium octane sulfonate, sodium xylene sulfonate, and ammonium octane sulfonate, as well as some phosphate esters.

Solvents

The preferred solvent for the present composition is water. However, one skilled in the art will recognize that solvents or co-solvents other than water may be used to serve the same purpose. In some embodiments, a composition may contain at least about 5% by weight water and preferably at least about 10% by weight water based on the total weight of the composition. Propylene glycol, ethylene glycol, glycerine and alcohols can also be used as solvents either alone or in combination with water.

Compositions according to the present compositions are generally acidic, and in certain embodiments, have a pH less than about 5, less than about 3.5, or less than about 3. In certain embodiments where the compositions are formulated as concentrates, the pH may be between about 0.1 to about 5, between about 1 to about 4, between about 1.25 to about 3.5, or between about 1.5 to about 3. In certain embodiments where the compositions are formulated as ready-to-use formulations or diluted from concentrates to form use solutions, the pH may be between about 1 to about 5, between about 1.5 to about 4, between about 1.5 to about 3.5, or between about 2 to about 3. Generally, however, the pH may be adjusted to any value that is desired in the intended environment of use by the addition of acid, base or buffer.

In certain embodiments, compositions according to the present invention exhibit excellent physical stability at the time of making, after extended storage periods, after low temperature exposure, and/or in the presence of organic soils. By "physical stability" it is meant that the composition remains a substantially homogenous solution and does not phase separate, e.g., produce precipitates or a separate layer of organic liquid. In particular embodiments, the compositions remain physically stable for storage periods of at least 3 months, at least 6 months, or at least one year at 25° C. Certain embodiments also exhibit these stability characteristics when stored for these periods at 10° C. In certain other embodiments, particularly when the germicidal composition is formulated as a ready-to-use solution or a use dilution, the compositions remain physically stable upon exposure to a temperature of 10° C. for 24 hours, or in the presence of 3 g/L bovine albumin solution. In still other embodiments, the compositions, particularly concentrate formulations, are formulated to exhibit excellent freeze-thaw stability, even through multiple freeze-thaw cycles. In particular embodiments, the compositions are capable of being frozen (preferably, maintained as a frozen solid for at least 24 hours) and then thawed into the liquid state and remain substantially homogeneous (i.e., no discernable phase separation). Even after a total of two, three, four or more such freeze-thaw cycles, the thawed composition may comprise a substantially homogeneous solution.

As noted above, compositions according to the present invention may be initially formulated as a concentrate and diluted with water to form a use solution. In certain embodiments, use solutions may be formulated by mixing one part of a concentrate formulation made in accordance with the present invention with between about 1 to about 100 parts water, between about 20 to about 75 parts water, or between about 30 to about 60 parts water. Thus, in certain embodiments, the use solutions are predominantly aqueous comprising greater than 90% by weight water, greater than 95% by weight water, or greater than 98% by weight water.

The present invention also provides methods for treating or preventing infectious hoof diseases comprising topically administering to the hooves of an animal a therapeutically effective amount of a composition made in accordance with the present invention described herein. The phrase "therapeutically effective amount" is intended to qualify the amount of the topical composition which will achieve the goal of decreased microbial concentration. "Therapeutically effective" may also refer to improvement in disorder severity or the frequency of incidence over no treatment.

Advantageously, the resulting germicidal compositions described herein may be used to treat animal hooves that are presented in their natural state. Hooves in their natural state may be soiled with particulate matter, such as dirt and manure, and/or microscopic pathogens, such as bacteria. For example, the present compositions remain antimicrobially effective in the presence of greater than 10% manure, or greater than 20% manure, as determined by in vitro testing using a modified EN 1040 micro-testing procedure. According to this modified procedure, manure collected from a dairy farm is dispensed into Erlenmeyer flasks, homogenized and autoclaved at 121° C. for 30 minutes. Manure samples are then stored in a freezer until needed. For testing, the manure samples are thawed to room temperature, and dispensed into testing tubes for the desired challenge against bacteria species such as *E. coli* and *S. aureus*. The test is performed at 10° C. Thus, in certain embodiments, methods according to the present invention eliminate the need for a hoof pre-treatment or pre-washing step to remove a substantial portion of the organic soils prior to application of the germicidal composition. The elimination of this step provides significant cost and time savings over known compositions and hoof treatment methods. Under normal conditions in dairy farms hoof cleaning methods if employed are less than 100% effective if removing soil from hooves. Compositions of the present invention demonstrate improved efficacy when hooves are only partially cleaned.

The germicidal compositions may be administered to the animal as a liquid, a spray, a foam, a gel, an ointment, a cream, a footbath, a footwrap coated with the composition, or any other acceptable topical form.

The germicidal compositions are particularly effective in the treatment and prevention of hoof diseases such as papillomatous digital dermatitis, interdigital phlegmon, interdigital dermatitis, laminitis, white line disease, and heel erosion. As a number of hoof diseases are highly contagious and are capable of being spread throughout an entire herd, prophylactic use of the germicidal compositions, even on animals with healthy hooves, can be an important practice in maintaining herd health. However, if cases of infections are discovered, the germicidal compositions are also effective in treating existing lesions and infections in affected animals.

Certain germicidal compositions according to the present invention are capable of providing a substantial reduction in Gram positive and Gram negative bacterial populations. In such embodiments, the reduction in bacteria population levels is greater than 99%, greater than 99.9%, greater than 99.99%, or greater than 99.999%. Exemplary bacteria that contribute to hoof infections and which may be treated with compositions according to the present invention include *Bacteroides* spp, *Bacteroides melaningenicus*, *Campylobacter faecalis*, *Clostridium* spp, *Fusobacterium* spp, *Peptococcus asaccharolyticus*, *Peptostreptococcus* spp, *Serpens* spp, *Treponema* spp, *Bacteroides thetaictaomicron*, *Fusobacterium necrophorum*, *Prevotella melaminogenicus*, *Porphyromonas asaccharolytica*, *Porphyromonas levii*, *Porphyromonas melaminogenicus*, *Dichelobacter fragilis*, *Arcanobacterium pyogenes*, *Dichelobacter nodosus*, and *Porphyromonas necrophorum*. The quantity of a composition that achieves a substantial reduction in a bacterial population is considered an effective amount of the composition for treating or preventing infectious hoof diseases. The compositions of this invention will also help control other environmental bacteria such as *E. coli* that may be present in PDD lesions or skin dwelling bacteria such as *S. aureus*. This bacteria can cause secondary infections once a PDD lesion is formed.

A broader purpose of the disclosed instrumentalities of the present invention is to provide a germicidal composition that may be used for any application requiring antibacterial or bactericidal properties. In a particular embodiment, the composition is formulated for use as a footbath for treating animal hooves. In other embodiments, the composition may be formulated for use as a hand sanitizer, a skin cleanser, a surgical scrub, a wound care agent, a disinfectant, a bath/shower gel, a hard surface sanitizer and the like. It will be understood, however, that different uses may prompt different pH targets. For example, compositions adapted for hard surfaces may exhibit low pH values, such as 1.0 or 0.5.

EXAMPLES

The following examples set forth exemplary compositions according to the present invention along and data regarding the antimicrobial efficacy of the same. It is to be understood, however, that these examples are provided by way of illustration and nothing therein should be taken as a limitation upon the overall scope of the invention.

Example 1

In this experiment, the efficacy of three experimental hoofbath products in the prevention of digital dermatitis (DD) and heel erosion (HE), relative to 5% copper sulfate (positive control; CTL) was studied. Eight lactating pens containing approximately 450 cows each from a 10,000 cow dairy were used in this study with two pens assigned to each treatment group. A total of 4,961 cows from all lactations were enrolled in the study. The trial lasted for a total of 3 months. Hoofbaths were used five days a week (Monday to Friday), once a day. There were six parlor evaluations three weeks apart of the rear hooves of cows enrolled in the study. The first two evaluations were conducted before the initiation of the implementation of the hoofbath treatments, and the other four evaluations during the study. The evaluations were performed at the parlor and hind feet of cows were scored for DD and HE immediately after washing with a water hose. The κ M-stage scoring system was used for DD and the presence or absence of HE was recorded for each foot. Outcomes evaluated included incidence of DD and HE during the study, prevalence of all (old and new cases) and incidence of DD and HE at each one of the four evaluation visits. It was concluded that experimental treatments were as effective or more effective (depending on the parameter evaluated) than CTL to reduce the incidence and prevalence of DD and HE.

TABLE 1

Formulations Tested

| | | Concentrates | | | Ready to use dilutions | | |
|---|---|---|---|---|---|---|---|
| Ingredients | % active | A % w/w | B % w/w | C % w/w | A % w/w | B % w/w | C % w/w |
| Acetic Acid | 100% | — | 4.00 | 4.00 | — | 0.1 | 0.1 |
| Formic Acid | 85% | 10.22 | 17.78 | 17.78 | 0.23 | 0.4 | 0.4 |
| Lactic Acid | 88% | 10.91 | — | — | 0.24 | — | — |
| $H_3PO_4$ | 75% | — | 9.07 | 0.00 | — | 0.17 | — |
| α-olefin sulfonate* | 40% | 58.00 | 60.00 | 60.00 | 0.58 | 0.6 | 0.6 |
| NEODOL 91-6** | 100% | — | 8.00 | 8.00 | — | 0.2 | 0.2 |
| Water | | 20.87 | 1.16 | 10.22 | 98.95 | 98.53 | 98.7 |
| pH | | 1.89 | <1 | 1.81 | 2.32 | 1.97 | 2.31 |

*WITCONATE AOS, Sodium C14-16 Olefin Sulfonate
**Primary alcohol ethoxylate available from Shell Chemicals Digital Dermatitis The results of the DD visit prevalence are shown in Table 2. "Relative Risk" is a ratio of the probability of developing a disease for two different groups. A value of less than 1 indicates a smaller risk of the disease incidence in the test group versus the control group. At the cow level, the study incidence risk (not shown) and visit prevalence of DD was lower (P<0.05) for treatment A than for CTL. Comparing experimental products, treatment A was superior to treatment B and non-inferior (i.e., performed at least as well as) to treatment C. Treatment C was non-inferior to treatment B.

TABLE 2

Digital Dermatitis (DD) visit prevalence for the different treatments - Cow Level

| Treatments | Relative Risk | Superiority/ Inferiority 95% CI | | P-value | Result[1] |
|---|---|---|---|---|---|
| A/CTL | 0.76 | 0.61 | 0.94 | 0.01 | S |
| B/CTL | 0.96 | 0.78 | 1.17 | 0.66 | NI Δ13% |
| C/CTL | 0.82 | 0.66 | 1.01 | 0.06 | NI Δ0% |

TABLE 2-continued

Digital Dermatitis (DD) visit prevalence for the different treatments - Cow Level

| Treatments | Relative Risk | Superiority/ Inferiority 95% CI | | P-value | Result[1] |
|---|---|---|---|---|---|
| A/B | 0.79 | 0.64 | 0.99 | 0.04 | S |
| A/C | 0.93 | 0.74 | 1.16 | 0.51 | NI Δ12% |
| C/B | 0.86 | 0.70 | 1.06 | 0.16 | NI Δ2% |

[1]S = significant at the P < 0.05 level; NI = non-inferior, plus the percent change between the two treatments FIG. 1 is a Kaplan-Meier survival graph illustrating the results of this study in terms of the probably of DD at the cow level at different times after enrollment. Treatment A exhibited clear superiority over the control for each time interval.

Figure 2:
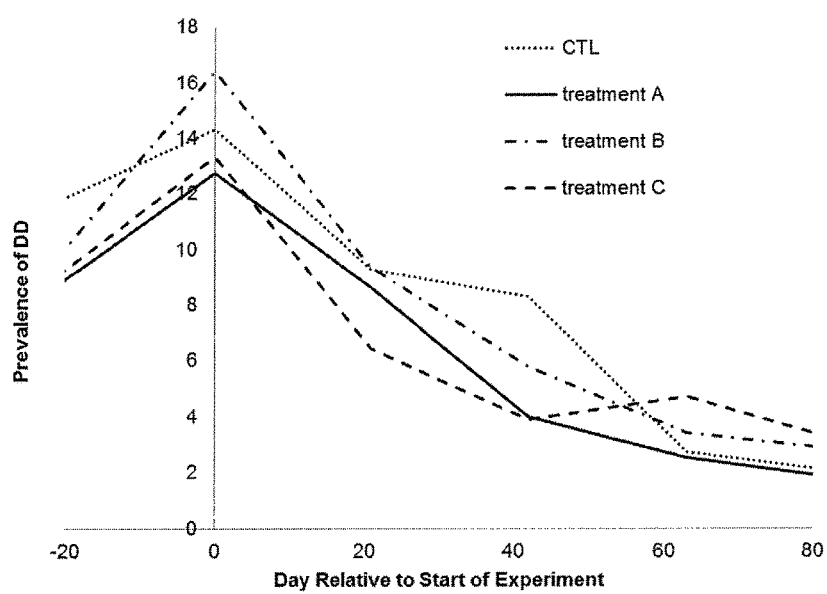
FIG. 2 is a chart illustrating DD prevalence at the cow level at different times after enrollment.

FIG. 2 is a graph illustrating DD prevalence at the cow level at different times after enrollment. The data collected prior to start of the trials (time zero) shows that a rise in DD prevalence in the study group. After treatments began, the DD prevalence decreased considerably with the DD prevalence in cows treated with A, B, and C tracking very closely with the control.

Heel Erosions

The results of the HE visit prevalence evaluation are reported in Table 3. At the cow level, the incidence (not shown), all cases and new cases, and prevalence of HE was lower (P<0.05) for formula A and C than for CTL. Formula B was non-inferior to CTL.

TABLE 3

Heel erosions (HE) prevalence for the different treatments

| | | Treatment Effect | | | |
|---|---|---|---|---|---|
| Treatment | Relative Risk | Superiority/ Inferiority 95% CI | | P-value | Result[1] |
| A/CTL | 0.52 | 0.31 | 0.84 | 0.01 | S |
| B/CTL | 0.72 | 0.46 | 1.08 | 0.11 | NI Δ10% |
| C/CTL | 0.49 | 0.28 | 0.81 | <0.01 | S |
| A/B | 0.74 | 0.43 | 1.20 | 0.23 | NI Δ8% |
| A/C | 1.06 | 0.60 | 1.69 | 0.84 | NI Δ58% |
| C/B | 0.72 | 0.49 | 1.16 | 0.17 | NI Δ7% |

Figure 3:
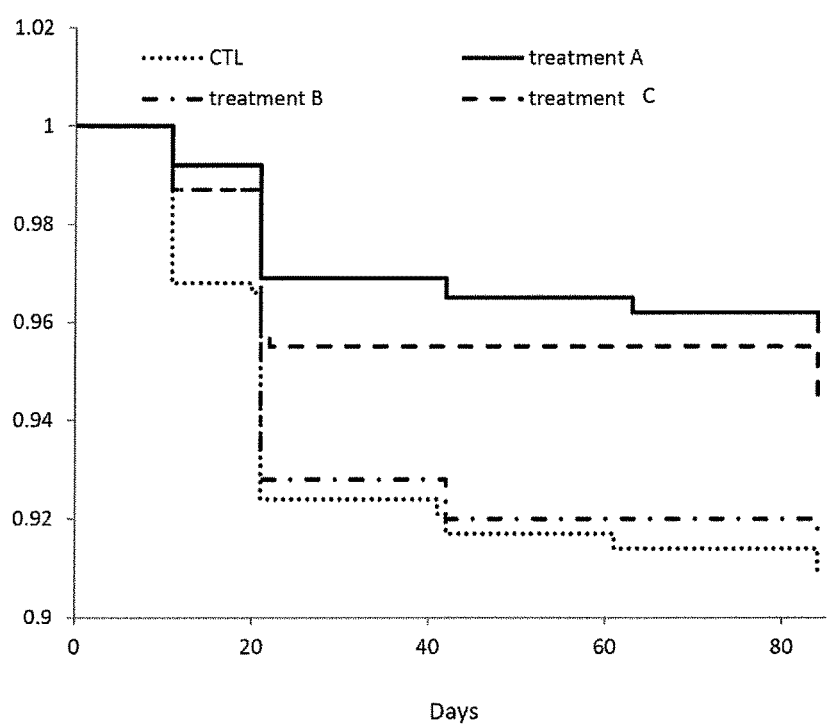
FIG. 3 is a Kaplan-Meier survival graph illustrating the results of a heel erosion (HE) study in terms of the probably of HE at the cow level at different times after enrollment.

[1]S = significant at the P < 0.05 level; NI = non-inferior, plus the percent change between the two treatment FIG. 3 is a Kaplan-Meier survival graph representing the probability of HE at the cow level at different times after enrollment. Treatments A and C exhibited significant superiority over the control for the time periods shown. Treatment B was established to be non-inferior compared to the control. Therefore, the experimental treatments prove to be just as effective, and in some instances significantly more effective, than the control in treating HE.

Figure 4:
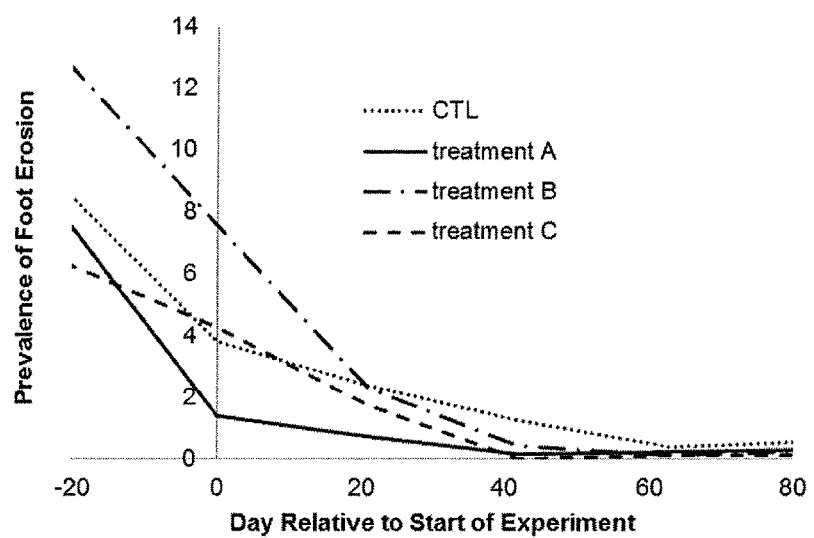
FIG. 4 is a chart illustrating HE prevalence at the cow level at different times after enrollment.

FIG. 4 is a graph illustrating HE prevalence at the cow level at different times after enrollment. DD prevalence in cows treated with A, B, and C decreased considerably after treatments began and tracked very closely with the control.

In Vitro Micro-Efficacy

The in vitro efficacy of each of the experimental formulations was tested for Treponeme cells, *Escherichia coli, Staphylococcus aureus, Pseudomonas aeruginosa,* and *Enterococcus hirae.*

The minimum inhibitory concentration (MIC) for Treponeme cells was determined. Treponeme cells were grown in an anaerobic chamber for at least 5-7 days at 37° C. until ~90% of the culture was in the spirochete form. A 96-well microtiter plate (12 columns×8 rows) was used for the studies. The first column of the plate was filled with 100 mL of the germicidal formulations, the second through 12$^{th}$ column were filled with 100 mL of saline or OTEB (Oral Treponeme Media). Subsequently, columns 2-11 were used to prepare series of ½ dilutions of biocide in OTEB media, and column 12 was assigned for growth control. To each cell a suspension of Treponeme cells was added. The cells were in contact with biocide for 5 minutes contact time, and then 3 mL were transferred onto Fastidious Anaerobe Agar plate. The plates were incubated at 37° C. for 5-7 days until visible growth appeared in column 12. At this time the MIC (and MBC) scores were collected.

Modified EN1040 and EN1656 Testing

The germicidal efficacy in the presence of manure was determined using a modified EN 1040 micro-testing procedure. According to this test, manure was collected from a dairy farm, dispensed into Erlenmeyer flasks, homogenized and autoclaved at 121° C. for 30 minutes. Manure samples were then stored in the freezer until needed. For testing, the manure samples were thawed to room temperature, and dispensed into testing tubes for the desired challenge. The test was performed at 10° C., with bacteria species *E. coli* and *S. aureus.*

The EN1656 standardized test procedure was also used for efficacy testing at 10° C., under simulated low soil conditions (3 g/L bovine albumin solution) for the four selected test organisms: *E. coli, S. aureus, P. aeruginosa,* and *E. hirae.* In addition to the required 30 minutes contact time, shorter contact times were tested as well. The results reported in Table 4 are for a contact time of only 30 seconds.

TABLE 4

In vitro micro-efficacy results

| | Formula | | |
|---|---|---|---|
| Micro Testing Conditions | A | B | C |
| Treponema (ppm, MIC) | 294 | 156 | 313 |
| Modified EN1040 - 10° C., 20% manure, 30 sec, S. aureus ("A" repeated twice) | 5.5/5.2 | 4.2 | 4.4 |
| Modified EN1040 - 10° C., 20% manure, 30 sec, E. coli ("A" repeated twice) | 5.5/4.6 | 4.5 | 4.5 |
| EN1656 - 10° C., low soil, 30 sec, S. aureus | 6.7* | 6.7* | 6.7* |
| EN1656 - 10° C., low soil, 30 sec, E. coli | 6.7* | 6.7* | 6.7* |
| EN1656 - 10° C., low soil, 30 sec, P. aeruginosa | 6.2* | 6.2* | 6.2* |
| EN1656 - 10° C., low soil, 30 sec, E. hirae | 6.3* | 6.3* | 5.0 |

*Indicates complete kill

Example 2

In this example, additional exemplary concentrate and use solution compositions in accordance with the present invention are described, and the in vitro efficacy of those use solutions are reported.

Table 5 discloses various use solutions, 1-6, and in vitro efficacy (log kill) testing thereof against *S. aureus, P. aeruginosa, E. hirae,* and *P. hauseri* under EN1656. Also, efficacy testing against *E. coli* and *S. aureus* under the AOAC sanitizer test (Association of Official Analytical Chemists. 1990. Official Methods of Analysis, Pages 138-140 in Germicidal and Detergent Sanitizing Action of Disinfectants 960.09, Vol. I. 15th ed. AOAC, Arlington, Va.) is reported. As can be seen, all formulations exhibited greater than a 5 log reduction for all organisms tested.

TABLE 5

| Ingredient | Formulation | | | | | |
|---|---|---|---|---|---|---|
| | 1 | 2 | 3 | 4 | 5 | 6 |
| α-olefin sulfonate (WITCONATE AOS) | 0.6 | 0.6 | 0.6 | 0.6 | 0.6 | 0.6 |
| Lactic acid | 0.4 | 0.25 | 0.1 | — | — | — |
| Citric acid | — | — | — | — | 0.4 | 0.1 |
| Acetic acid | — | — | — | 0.25 | — | — |
| Formic acid | 0.1 | 0.25 | 0.4 | 0.25 | 0.1 | 0.4 |
| NEODOL 91-6 | — | — | — | — | 0.1 | 0.2 |
| Water | 98.9 | 98.9 | 98.9 | 98.9 | 98.8 | 98.7 |
| pH | 2.35 | 2.34 | 2.32 | 2.46 | 2.34 | 2.32 |
| EN 1656 S. aureus, low soil, 5 min, 10° C. | 5.9 | 5.9 | 5.9 | 5.9 | 5.9 | 5.9 |
| EN 1656 P. aeruginosa, low soil, 5 min, 10° C. | 6.2 | 6.2 | 6.2 | 6.2 | 6.2 | 6.2 |
| EN 1656 E. hirae, low soil, 5 min, 10° C. | 6.0 | 6.0 | 6.0 | 6.0 | 6.0 | 6.0 |
| EN 1656 P. hauseri, low soil, 5 min, 10° C. | 5.9 | 5.9 | 5.9 | 5.9 | 5.3 | 5.9 |
| AOAC, 5 min, 10% manure, E. coli | 5.7/5.1 | 6.9/5.2 | 6.9/5.3 | 5.0 | 5.7 | 5.8 |
| AOAC, 5 min, 10% manure, S. aureus | 6.8/6.3 | 6.8/6.4 | 6.8/5.4 | 5.5 | 6.8 | 5.9 |

Table 6 discloses various concentrate formulations in accordance with the present invention and their corresponding ready-to-use (RTU) solutions. The dilution ratio (part concentrate+parts water) is given in parentheses. The in vitro efficacy of the use dilution formulations was determined by testing against S. aureus, P. aeruginosa, E. hirae, and P. hauseri under EN1656. Also, efficacy testing against E. coli and S. aureus under the AOAC sanitizer test is reported. As can be seen, all formulations exhibited greater than a 5 log reduction for all organisms tested.

TABLE 6

| Ingredients | Activity | 7 | | 8 | | 9 | | 10 | | 11 | |
|---|---|---|---|---|---|---|---|---|---|---|---|
| | | Conc. | RTU (1 + 49) | Conc. | RTU (1 + 49) | Conc. | RTU (1 + 39) | Conc. | RTU (1 + 49) | Conc. | RTU (1 + 49) |
| Lactic acid | 88% | — | — | — | — | — | — | 13.5 | 0.24 | 5 | 0.1 |
| Formic acid | 85% | 5.88 | 0.1 | 22.5 | 0.4 | 11.76 | 0.25 | 13.5 | 0.23 | 23 | 0.4 |
| Acetic acid | 100% | 20 | 0.4 | 4.5 | 0.1 | — | — | — | — | — | — |
| Citric acid | 100% | — | — | — | — | 10 | 0.25 | — | — | — | — |
| α-olefin sulfonate | 40% | 74.12 | 0.6 | 73 | 0.6 | 60 | 0.6 | 73 | 0.6 | 72 | 0.6 |
| NEODOL 91-6 | 100% | — | — | — | — | 4 | 0.1 | — | — | — | — |
| pH | | 2.24 | 2.69 | 1.5 | 2.24 | 1.58 | 2.38 | 1.69 | 2.31 | 1.61 | 2.27 |
| AOAC Log reduction - 5 min, 10% manure, 10° C. | E. coli | 5.4 | | 6.0 | | 6.9 | | 6.9/5.2 | | 6.9/5.3 | |
| | S. aureus | 5.9 | | 6.8 | | 6.8 | | 6.8/6.4 | | 6.8/5.4 | |
| EN1656 Log reduction - 5 min, low soil, 10° C. | P. aeruginosa | 6.2 | | 6.2 | | 6.2 | | 6.2 | | 6.2 | |
| | S. aureus | 5.9 | | 5.9 | | 5.9 | | 5.9 | | 5.9 | |
| | E. hirae | 6.0 | | 6.0 | | 6.0 | | 6.0 | | 6.0 | |
| | P. hauseri | 5.9 | | 5.9 | | 5.9 | | 5.9 | | 5.9 | |

It was discovered that certain physical characteristics of the concentrate and use solution formulations, such as physical stability and freezing point, could be improved through the use of various surfactant blends. Tables 7 and 8 also disclose various concentrate formulations in accordance with the present invention and their corresponding ready-to-use (RTU) solutions. The dilution ratio (part concentrate+parts water) is given in parentheses. The in vitro efficacy of the use dilution formulations was determined by testing against E. coli and S. aureus under the AOAC sanitizer test.

In Table 7, it is shown that the addition of sodium lauryl sulfate as a further secondary anionic surfactant (with sodium α-olefin sulfonate being the majority or primary anionic surfactant and sodium octane sulfonate being another secondary surfactant) did not adversely impact germicidal efficacy while improving the stability of the formulation (observed). Further the addition of propylene glycol in place of added water had the effect of reducing the freezing point of the formulation in the presence of light organic soil (3 g/L bovine albumin) (observed), while boosting the germicidal efficacy against E. coli. In addition, Table 7 shows the use of AEROSOL OT 75 (dioctyl sodium sulfosuccinate) in place of sodium lauryl sulfate without an adverse impact on germicidal efficacy. Moreover, addition of a small amount of NEODOL 91-8 alcohol ethoxylate could also be added without an adverse impact on germicidal efficacy. The alcohol ethoxylate also had the benefit of improving solubility of the other surfactants at low temperature (observed).

In Table 8, sodium laureth sulfate (2 and 3 moles ethylene oxide) and dioctyl sodium sulfosuccinate were used as the secondary anionic surfactants. Again, an amount of alcohol ethoxylate surfactant was also added without adversely affecting germicidal efficacy while improving the low temperature stability.

TABLE 7

| Ingredients | % active | 12 Conc. | 12 RTU (1 + 49) | 13 Conc. | 13 RTU (1 + 49) | 14 Conc. | 14 RTU (1 + 49) | 15 Conc. | 15 RTU (1 + 49) | 16 Conc. | 16 RTU (1 + 49) |
|---|---|---|---|---|---|---|---|---|---|---|---|
| α-olefin sulfonate | 40 | 31.5 | 0.25 | 31.5 | 0.25 | 31.5 | 0.25 | 43.34 | 0.35 | 40.34 | 0.32 |
| Sodium Octane sulfonate | 36 | 41.84 | 0.30 | 26.16 | 0.19 | 26.16 | 0.19 | 23.33 | 0.17 | 24.33 | 0.18 |
| Sodium Lauryl Sulfate | 30 | — | — | 10.46 | 0.06 | 10.46 | 0.06 | — | — | — | — |
| AEROSOL OT 75 | 75 | — | — | — | — | — | — | 6.67 | 0.10 | 6.67 | 0.10 |
| NEODOL 91-8 | 100 | — | — | — | — | — | — | — | — | 2 | 0.04 |
| Water | | — | — | — | — | 5.22 | — | — | — | — | — |
| Propylene Glycol | | — | — | — | — | 5.22 | 0.10 | — | — | — | — |
| Lactic acid | 90 | 13.06 | 0.24 | 13.06 | 0.24 | 13.06 | 0.24 | 13.06 | 0.24 | 13.06 | 0.24 |
| Formic acid | 85 | 13.5 | 0.23 | 13.5 | 0.23 | 13.5 | 0.23 | 13.5 | 0.23 | 13.5 | 0.23 |
| Dye | 100 | 0.1 | 0.002 | 0.1 | 0.002 | 0.1 | 0.002 | 0.1 | 0.002 | 0.1 | 0.002 |
| AOAC Log reduction, 10% manure, 1 min, 10° C. | S. aureus | 6.2 | | 6.2 | | 6.2 | | 6.0 | | 6.0 | |
| | E. coli | 4.2 | | 4.3 | | 5.3 | | 5.8 | | 5.4 | |

TABLE 8

| Ingredients | % active | 17 Conc. | 17 RTU (1 + 49) | 18 Conc. | 18 RTU (1 + 49) | 19 Conc. | 19 RTU (1 + 49) | 20 Conc. | 20 RTU (1 + 49) |
|---|---|---|---|---|---|---|---|---|---|
| α-olefin sulfonate | 40 | 37.83 | 0.30 | 37.83 | 0.30 | 37.83 | 0.30 | 37.83 | 0.30 |
| Sodium laureth sulfate (3 mol EO) | 28 | 28.84 | 0.16 | 26.84 | 0.15 | — | — | — | — |
| Sodium laureth sulfate (2 mol EO) | 28 | — | — | — | — | 28.84 | 0.16 | 26.84 | 0.15 |
| AEROSOL OT 75 | 75 | 6.67 | 0.10 | 6.67 | 0.10 | 6.67 | 0.10 | 6.67 | 0.10 |
| NEODOL 91-8 | 100 | — | — | 2 | 0.04 | — | — | 2 | 0.04 |
| Lactic acid | 90 | 13.06 | 0.24 | 13.06 | 0.24 | 13.06 | 0.24 | 13.06 | 0.24 |
| Formic acid | 85 | 13.5 | 0.23 | 13.5 | 0.23 | 13.5 | 0.23 | 13.5 | 0.23 |
| Dye | 100 | 0.1 | 0.002 | 0.1 | 0.002 | 0.1 | 0.002 | 0.1 | 0.002 |
| AOAC Log reduction, 10% manure, 1 min, 10° C. | S. aureus | 6.0 | | 6.0 | | 5.7 | | 5.7 | |
| | E. coli | 4.9 | | 5.1 | | 7.0 | | 7.0 | |

| Ingredients | % active | 21 Conc. | 21 RTU (1 + 49) | 22 Conc. | 22 RTU (1 + 49) | 23 Conc. | 23 RTU (1 + 49) | 24 Conc. | 24 RTU (1 + 49) |
|---|---|---|---|---|---|---|---|---|---|
| α-olefin sulfonate | 40 | 37.83 | 0.30 | 33.83 | 0.27 | 36.5 | 0.29 | 34.5 | 0.28 |
| Sodium laureth sulfate (3 mol EO) | 28 | — | — | — | — | — | — | — | — |
| Sodium laureth sulfate (2 mol EO) | 28 | 24.84 | 0.14 | 28.84 | 0.16 | 26.84 | 0.15 | 28.84 | 0.16 |
| AEROSOL OT 75 | 75 | 6.67 | 0.10 | 6.67 | 0.10 | 8 | 0.12 | 8 | 0.12 |
| NEODOL 91-8 | 100 | 4 | 0.08 | 4 | 0.08 | 2 | 0.04 | 2 | 0.04 |
| Lactic acid | 90 | 13.06 | 0.24 | 13.06 | 0.24 | 13.06 | 0.24 | 13.06 | 0.24 |
| Formic acid | 85 | 13.5 | 0.23 | 13.5 | 0.23 | 13.5 | 0.23 | 13.5 | 0.23 |
| Dye | 100 | 0.1 | 0.002 | 0.1 | 0.002 | 0.1 | 0.002 | 0.1 | 0.002 |
| AOAC Log reduction, 10% manure, 1 min, 10° C. | S. aureus | 5.7 | | 4.3 | | 5.7 | | 5.7 | |
| | E. coli | 5.5 | | 5.2 | | 5.6 | | 6.0 | |

Tables 9-11 set forth additional exemplary compositions according to the present invention, providing physical stability information for each under various conditions. Composition formulations are expressed in terms of actual levels of the stated component, already taking into account the composition or purity of the raw materials. Specifically, Table 9 discloses use dilution compositions comprising sodium lauryl sulfate (SLS), lactic acid, and formic acid. Table 10 discloses use dilution compositions comprising sodium α-olefin sulfonate (SAOS), lactic acid and formic acid. Table 11 discloses use dilution compositions comprising both SLS and SAOS, along with lactic and formic acids. All formulations exhibited at least some physical stability (i.e., no discernible precipitate). Certain particular formulations exhibited enhanced stability, even in the presence of light organic soils (3 g/L bovine albumin) and at low temperature (about 10° C.) for 24 hours after manufacture.

TABLE 9

| Ingredients | 25 % (w) | 26 % (w) | 27 % (w) | 28 % (w) | 29 % (w) | 30 % (w) | 31 % (w) | 32 % (w) | 33 % (w) | 34 % (w) | 35 % (w) | 36 % (w) |
|---|---|---|---|---|---|---|---|---|---|---|---|---|
| Lactic Acid | 0.4 | 0.25 | 0.1 | 0.4 | 0.25 | 0.1 | 0.4 | 0.25 | 0.1 | 0.4 | 0.25 | 0.1 |
| Formic Acid | 0.1 | 0.25 | 0.4 | 0.1 | 0.25 | 0.4 | 0.1 | 0.25 | 0.4 | 0.1 | 0.25 | 0.4 |
| SLS | 0.6 | 0.6 | 0.6 | 0.6 | 0.6 | 0.6 | 0.5 | 0.5 | 0.5 | 0.5 | 0.5 | 0.5 |
| NEODOL 91-6 | 0.1 | 0.1 | 0.1 | 0.2 | 0.2 | 0.2 | 0.1 | 0.1 | 0.1 | 0.2 | 0.2 | 0.2 |
| water, hard | 98.8 | 98.8 | 98.8 | 98.7 | 98.7 | 98.7 | 98.9 | 98.9 | 98.9 | 98.8 | 98.8 | 98.8 |
| Physical Stability at room temperature | OK | OK | OK | OK | OK | OK | OK | OK | OK | OK | OK | OK |
| Phys. Stab. w/ Low Soil | OK | OK | OK | OK | OK | OK | ppt | ppt | ppt | ppt | ppt | ppt |
| Phys. Stab. at 10° C. | Hazy | Hazy | Hazy | Hazy | Hazy | Hazy | — | — | — | — | — | — |

TABLE 10

| Ingredients | 37 % (w) | 38 % (w) | 39 % (w) | 40 % (w) | 41 % (w) | 42 % (w) | 43 % (w) | 44 % (w) | 45 % (w) | 46 % (w) | 47 % (w) | 48 % (w) | 49 % (w) |
|---|---|---|---|---|---|---|---|---|---|---|---|---|---|
| Lactic Acid | 0.4 | 0.25 | 0.1 | 0.4 | 0.25 | 0.1 | 0.4 | 0.25 | 0.1 | 0.4 | 0.25 | 0.1 | 0.4 |
| Formic Acid | 0.1 | 0.25 | 0.4 | 0.1 | 0.25 | 0.4 | 0.1 | 0.25 | 0.4 | 0.1 | 0.25 | 0.4 | 0.1 |
| SAOS | 0.6 | 0.6 | 0.6 | 0.6 | 0.6 | 0.6 | 0.6 | 0.6 | 0.6 | 0.5 | 0.5 | 0.5 | 0.5 |
| NEODOL 91-6 | 0 | 0 | 0 | 0.1 | 0.1 | 0.1 | 0.2 | 0.2 | 0.2 | 0 | 0 | 0 | 0.1 |
| water, hard | 98.9 | 98.9 | 98.9 | 98.8 | 98.8 | 98.8 | 98.7 | 98.7 | 98.7 | 99 | 99 | 99 | 98.9 |
| Physical Stability at room temperature | OK | OK | OK | OK | OK | OK | OK | OK | OK | OK | OK | OK | OK |
| Phys. Stab. w/ Low Soil | OK | OK | OK | ppt | ppt | slight ppt | ppt | ppt | ppt | ppt | ppt | ppt | ppt |
| Physical stability 10° C. | OK | OK | OK | OK | OK | OK | OK | OK | OK | OK | OK | OK | OK |

TABLE 11

| Ingredients | 50 % (w) | 51 % (w) | 52 % (w) | 53 % (w) | 54 % (w) | 55 % (w) | 56 % (w) | 57 % (w) | 58 % (w) | 59 % (w) | 60 % (w) | 61 % (w) | 62 % (w) | 63 % (w) |
|---|---|---|---|---|---|---|---|---|---|---|---|---|---|---|
| Lactic Acid | 0.25 | 0.1 | 0.4 | 0.25 | 0.1 | 0.4 | 0.25 | 0.1 | 0.4 | 0.25 | 0.1 | 0.4 | 0.25 | 0.1 |
| Formic Acid | 0.25 | 0.4 | 0.1 | 0.25 | 0.4 | 0.1 | 0.25 | 0.4 | 0.1 | 0.25 | 0.4 | 0.1 | 0.25 | 0.4 |
| SAOS | 0.5 | 0.5 | 0.5 | 0.5 | 0.5 | 0.5 | 0.5 | 0.5 | 0.3 | 0.3 | 0.3 | 0.1 | 0.1 | 0.1 |
| SLS | — | — | — | — | — | 0.1 | 0.1 | 0.1 | 0.3 | 0.3 | 0.3 | 0.5 | 0.5 | 0.5 |
| NEODOL 91-6 | 0.1 | 0.1 | 0.2 | 0.2 | 0.2 | 0 | 0 | 0 | 0 | 0 | 0 | 0 | 0 | 0 |
| water, hard | 98.9 | 98.9 | 98.8 | 98.8 | 98.8 | 98.9 | 98.9 | 98.9 | 98.9 | 98.9 | 98.9 | 98.9 | 98.9 | 98.9 |
| Physical Stability | OK | OK | OK | OK | OK | OK | OK | OK | OK | OK | OK | OK | OK | OK |
| Phys. Stab. w/ Low Soil | ppt | ppt | ppt | ppt | ppt | OK | OK | OK | OK | OK | OK | OK | OK | OK |
| Physical stability 10° C. | OK | OK | OK | OK | OK | OK | OK | OK | OK | OK | OK | Fail | Fail | Fail |

Example 3

In this example, concentrates according to the present invention were prepared comprising various surfactants and the effect of those surfactants on the freeze-thaw stability of the samples was determined. The concentrates were prepared for an intended dilution ratio of 1 part concentrate to 39 parts water. Each formulation tested comprised 9.2 wt. % formic acid, 9.4 wt. % lactic acid, 23.2 wt. % sodium α-olefin sulfonate (SAOS), and 21 wt. % of the indicated surfactant, with water comprising the balance.

The samples of each formulation were placed in bottles filled to 1.5 inches from the top of the bottles. The bottles containing the samples were placed in a freezer for one day, and removed from the freezer and thawed the subsequent day. The homogeneity of each sample upon thawing was noted. A formulation was considered acceptable if a homogeneous solution was observed upon thawing. The results are given below in Table 12.

TABLE 12

| Additive | Physical Stability After 1 Freeze-Thaw Cycle |
|---|---|
| Control (no additive) | Non-homogeneous |
| TWEEN 80 (polysorbate 80) | Homogeneous |
| Sodium xylene sulfonate (40%) | Non-homogeneous |
| NEODOL 91-8 (alcohol ethoxylate) | Non-homogeneous |
| NEODOL 91-6 (alcohol ethoxylate) | Homogeneous |
| NEODOL 91-2.5 (alcohol ethoxylate) | Homogeneous |
| SLS (30%) | Homogeneous |
| Cocamidopropylbetaine | Non-homogeneous |

TABLE 12-continued

| Additive | Physical Stability After 1 Freeze-Thaw Cycle |
|---|---|
| Glucopon 600UP (50%) | Homogeneous |
| Sodium octane sulfonate | Non-homogeneous |

It is noted that the sample comprising SLS was returned to the freezer and the procedure repeated to complete four freeze-thaw cycles. The sample remained homogeneous after the fourth cycle.

Table 13 summarizes certain exemplary germicidal concentrates and ready-to-use formulations or use dilutions in accordance with the present invention in terms of broad, intermediate and narrow ranges for levels (wt. %) of certain components thereof. It is understood that these compositions are exemplary only and should not be taken as limiting the overall scope of the present invention.

TABLE 13

| Ingredients | Concentrates | | | RTU/Use Dilutions | | |
|---|---|---|---|---|---|---|
| Formic Acid | 2-35% | 4-30% | 6-25% | 0.05-5% | 0.1-2.5% | 0.2-1.25% |
| C2-C10 carboxylic acid | 2-35% | 4-30% | 6-25% | 0.05-5% | 0.1-2.5% | 0.2-1.25% |
| Anionic surfactant (total) | 3-60% | 5-55% | 20-50% | 0.1-5% | 0.25-2.5% | 0.5-1% |
| Non-ionic surfactant (total) | 0-20% | 1-15% | 2-10% | 0-5% | 0.05-2.5% | 0.1-1% |
| pH | 0.1-5 | 1-3.5 | 1.5-3 | 1-5 | 1.5-3.5 | 2-3 |

We claim:

1. An aqueous germicidal composition comprising:
   between 0.05% to 25% by weight of formic acid;
   one or more C2-C10 carboxylic acids; and
   two or more anionic surfactants, wherein an α-olefin sulfonate comprises at least 50% by weight of said anionic surfactants.

2. The composition according to claim 1, wherein said composition comprises between about 0.05% to about 35% by weight of said C2-C10 carboxylic acid.

3. The composition according to claim 1, wherein said one or more C2-C10 carboxylic acids are selected from the group consisting of acetic acid, lactic acid, citric acid, propionic acid, butyric acid, glycolic acid, gluconic acid, glutaric acid, adipic acid, aspartic acid, glutamic acid, tartaric acid, pyruvic acid, fumaric acid, sorbic acid, maleic acid, malic acid, caprylic acid, perlagonic acid, and capric acid.

4. The composition according to claim 1 wherein said α-olefin sulfonate surfactant is a sodium C8-C18 α-olefin sulfonate.

5. The composition according to claim 1, wherein said two or more anionic surfactants are present in said composition at a level of between about 0.1% to about 60% by weight.

6. The composition according to claim 1, wherein said composition has a pH of less than 5.

7. The composition according to claim 1, wherein said composition further comprises a non-ionic surfactant.

8. The composition according to claim 7, wherein said non-ionic surfactant comprises an alcohol ethoxylate.

9. The composition according to claim 1, wherein said composition further comprises one or more members selected from the group consisting of pH adjusting agents, wetting agent, foaming agents, dyes, viscosity control agents, preservatives, skin conditioners, coupling agents, and solvents.

10. The composition according to claim 1, wherein said composition further comprises one or more germicides selected from the group consisting of N,N-bis(3-aminopropyl) $C_6$-$C_{18}$ alkyl amines, bronopol, chlorhexidine salts, triclosan, glycolic acid, polyhexamethyl biguanide, polyhexamethylene guanidine hydrochloride, polyhexamethylene guanidine hydrophosphate, poly[2-(2-ethoxy)-ethoxyethyl]-guanidinium chloride, benzyl alcohol, and benzoic acid.

11. The composition according to claim 1, wherein said composition comprises a homogeneous solution that remains physical stable for extended storage periods of at least 3 months at 25° C.

12. A germicidal use solution for treatment or prevention of hoof diseases comprising 1 part by weight of the aqueous composition according to claim 1 diluted with between about 1 to about 100 parts by weight water.

13. The use solution of claim 12, wherein said use solution remains physically stable upon exposure to a temperature of 10° C. for 24 hours, or in the presence of 3 g/L bovine albumin solution.

14. An aqueous germicidal composition comprising:
   between 0.05% to 25% by weight of formic acid;
   between about 0.05% to about 35% by weight of one or more carboxylic acids selected from the group consisting of acetic acid, lactic acid, and citric acid; and
   two or more anionic surfactants, wherein an α-olefin sulfonate comprises at least 50% by weight of said anionic surfactants,
   wherein upon testing under AOAC 960.09 standards at 10° C., 1 minute contact time, and in the presence of 10% manure, the composition exhibits at least a 5-log reduction in *Escherichia coli* and *Staphylococcus aureus*.

15. A method for treating or preventing infectious hoof diseases comprising topically administering a therapeutically effective amount of a composition according to claim 1 to the hooves of an animal.

16. The method according to claim 15, wherein said animal hooves have not undergone a pre-washing step prior to administration of said composition thereto.

17. The method according to claim 15, wherein said animal hooves, prior to administration of said composition thereto, include organic soils thereon.

18. The method according to claim 17, wherein said organic soils comprise manure.

19. The method according to claim 15, wherein said composition is diluted with water to form a use solution prior to administration to said animal hooves.

20. The method according to claim 15, wherein the hoof disease is selected from papillomatous digital dermatitis, interdigital phlegmon, interdigital dermatitis, laminitis, white line disease, and heel erosion.

21. The method according to claim 15, wherein said composition is administered as one of a spray, a foam, a gel, an ointment, a cream, a footbath or a footwrap.

\* \* \* \* \*